United States Patent
Osada et al.

(10) Patent No.: US 10,338,005 B2
(45) Date of Patent: Jul. 2, 2019

(54) APPARATUS FOR INSPECTING BACK SURFACE OF EPITAXIAL WAFER AND METHOD OF INSPECTING BACK SURFACE OF EPITAXIAL WAFER USING THE SAME

(71) Applicant: SUMCO CORPORATION, Tokyo (JP)

(72) Inventors: Tatsuya Osada, Tokyo (JP); Hideaki Kinbara, Tokyo (JP); Masahiko Egashira, Tokyo (JP)

(73) Assignee: SUMCO CORPORATION, Tokyo (JP)

( * ) Notice: Subject to any disclaimer, the term of this patent is extended or adjusted under 35 U.S.C. 154(b) by 0 days.

(21) Appl. No.: 15/765,349

(22) PCT Filed: Aug. 3, 2016

(86) PCT No.: PCT/JP2016/003583
§ 371 (c)(1),
(2) Date: Apr. 2, 2018

(87) PCT Pub. No.: WO2017/061063
PCT Pub. Date: Apr. 13, 2017

(65) Prior Publication Data
US 2018/0306731 A1 Oct. 25, 2018

(30) Foreign Application Priority Data
Oct. 5, 2015 (JP) .................................. 2015-197776

(51) Int. Cl.
*G01N 11/00* (2006.01)
*G01N 21/00* (2006.01)
(Continued)

(52) U.S. Cl.
CPC ......... *G01N 21/9501* (2013.01); *G01B 11/30* (2013.01); *G01N 21/8806* (2013.01);
(Continued)

(58) Field of Classification Search
None
See application file for complete search history.

(56) References Cited

U.S. PATENT DOCUMENTS

| | | | | |
|---|---|---|---|---|
| 4,450,358 A | * | 5/1984 | Reynolds | .................. G03F 9/70 219/121.61 |
| 4,505,585 A | * | 3/1985 | Yoshikawa | ........ G11B 7/00375 356/237.2 |

(Continued)

FOREIGN PATENT DOCUMENTS

| | | |
|---|---|---|
| JP | S63-124942 A | 5/1988 |
| JP | H07-249665 A | 9/1995 |

(Continued)

OTHER PUBLICATIONS

U.S. Appl. No. 15/757,856 to Tatsuya Osada et al., filed Mar. 6, 2018.

(Continued)

*Primary Examiner* — Shawn Decenzo
(74) *Attorney, Agent, or Firm* — Greenblum & Bernstein, P.L.C.

(57) ABSTRACT

Provided is an apparatus for inspecting the back surface of an epitaxial wafer, capable of detecting defects in the back surface of an epitaxial wafer. An epitaxial wafer back surface inspection apparatus has an optical system including an annular fiber optic illuminator and an imaging unit which are placed perpendicular to the back surface of an epitaxial wafer; and a scanning unit operating the optical system in parallel with the back surface to scan the back surface. A light source of the annular fiber optic illuminator is composed of either blue LEDs or red LEDs.

9 Claims, 12 Drawing Sheets

(51) Int. Cl.
  *G01N 21/95* (2006.01)
  *G01B 11/30* (2006.01)
  *G01N 21/956* (2006.01)
  *G01N 21/88* (2006.01)
  *G01N 21/84* (2006.01)

(52) U.S. Cl.
  CPC ... *G01N 21/956* (2013.01); *G01N 2021/8477* (2013.01); *G01N 2021/8845* (2013.01)

(56) References Cited

U.S. PATENT DOCUMENTS

| | | | | |
|---|---|---|---|---|
| 5,609,780 | A * | 3/1997 | Freedenberg | G01J 1/4257 219/121.73 |
| 5,841,893 | A * | 11/1998 | Ishikawa | G01N 21/88 382/145 |
| 6,002,262 | A * | 12/1999 | Higashi | G01B 7/345 257/E21.53 |
| 6,147,357 | A * | 11/2000 | Nicolesco | G01N 21/8806 250/228 |
| 6,700,606 | B1 * | 3/2004 | Borza | G06K 9/00013 348/218.1 |
| 6,825,487 | B2 * | 11/2004 | Preece | G01N 21/21 250/559.4 |
| 7,583,833 | B2 * | 9/2009 | McIntyre | G05B 23/0229 324/537 |
| 7,754,502 | B1 * | 7/2010 | Yegnashankaran | H01L 22/12 250/559.4 |
| 7,968,354 | B1 * | 6/2011 | Haller | G01N 21/9501 257/E21.521 |
| 8,339,593 | B2 | 12/2012 | Kamiyama et al. | |
| 8,411,263 | B2 * | 4/2013 | Uchino | G01N 21/6456 356/237.2 |
| 9,031,810 | B2 * | 5/2015 | Chen | H01L 22/12 356/237.1 |
| 9,633,913 | B2 * | 4/2017 | Mori | G01N 21/9501 |
| 2001/0055689 | A1 * | 12/2001 | Park | C30B 15/14 428/446 |
| 2002/0025480 | A1 * | 2/2002 | Itoh | G03F 1/32 430/5 |
| 2003/0164942 | A1 * | 9/2003 | Take | G01N 21/9501 356/237.2 |
| 2004/0021097 | A1 * | 2/2004 | Preece | G01N 21/21 250/559.4 |
| 2004/0115905 | A1 * | 6/2004 | Barge | H01L 21/306 438/473 |
| 2004/0246472 | A1 * | 12/2004 | Holsteyns | G01N 21/8422 356/237.1 |
| 2005/0213085 | A1 * | 9/2005 | Lee | G01N 21/9501 356/237.2 |
| 2006/0244955 | A1 * | 11/2006 | Schramm | B23K 31/12 356/237.2 |
| 2008/0018887 | A1 * | 1/2008 | Chen | G01N 21/47 356/237.2 |
| 2009/0197358 | A1 * | 8/2009 | Inami | H01L 22/24 438/16 |
| 2009/0304261 | A1 * | 12/2009 | Takahashi | G01N 21/9501 382/149 |
| 2013/0271596 | A1 * | 10/2013 | Lewis | G01N 21/8806 348/126 |

FOREIGN PATENT DOCUMENTS

| | | | |
|---|---|---|---|
| JP | 2007-067102 A | | 3/2007 |
| JP | 2007-292641 A | | 11/2007 |
| JP | 2010103275 | * | 2/2010 |
| JP | 2010-103275 A | | 5/2010 |
| JP | 2010127897 | * | 5/2010 |
| JP | 2010-127897 A | | 6/2010 |
| JP | 2015-513111 A | | 4/2015 |

OTHER PUBLICATIONS

International Search Report issued in WIPO Patent Application No. PCT/JP2016/003583, dated Oct. 18, 2016.

Office Action issued in Taiwan family member Patent Appl. No. 105125394, dated Oct. 18, 2017, along with an English translation thereof.

International Preliminary Report on Patentability issued in WIPO Patent Application No. PCT/JP2016/003583, dated Apr. 10, 2018.

Office Action issued in Japanese family member Patent Appl. No. 2015-197776, dated Jan. 8, 2019, along with an English translation thereof.

* cited by examiner

D3

Intensity

Position

APPARATUS FOR INSPECTING BACK SURFACE OF EPITAXIAL WAFER AND METHOD OF INSPECTING BACK SURFACE OF EPITAXIAL WAFER USING THE SAME

TECHNICAL FIELD

This disclosure relates to an apparatus for inspecting the back surface of an epitaxial wafer and a method of inspecting the back surface of an epitaxial wafer using the apparatus. This disclosure relates in particular to an apparatus for inspecting the back surface of an epitaxial wafer, capable of detecting and identifying defects formed in the back surface of an epitaxial wafer.

BACKGROUND

As substrates used in the production process of semiconductor devices, wafers made of a semiconductor such as silicon wafers are widely used. As for such a wafer, polished wafers (PWs) obtained by slicing a single crystal ingot and mirror polishing the slices, epitaxial wafers obtained by forming an epitaxial layer on a surface of a PW, and the like are known. For example, epitaxial wafers are used as device substrates of various semiconductor devices such as metal oxide semiconductor field-effect transistors (MOSFETs), dynamic random access memories (DRAMs), power transistors, and back-illuminated solid-state imaging devices. Note that while "epitaxial wafer surface", "front surface", or simply "surface" of an epitaxial wafer herein refers to one side of the main surfaces of an epitaxial wafer, where an epitaxial layer is formed. Whereas, "epitaxial wafer back surface" or "back surface" of the epitaxial wafer refers to the other side of the main surfaces of the epitaxial wafer, opposite to the surface where the epitaxial layer is formed (i.e., surface where the epitaxial layer is not formed).

In terms of enhancing yield and reliability of semiconductor device manufacturing processes, inspection techniques for detecting defects in the front and back surfaces of wafers used as substrates for semiconductor devices have increasingly become very important. Various defects are formed in the front and back surfaces of a wafer. Examples include crystal defects such as pits and COPs, unevenly polished portions and scratches formed due to machining, and adhesion of particles that constitute foreign matter.

Conventionally, using a light point defect (LPD) inspection apparatus (laser surface inspection system), wafer inspection is performed in which wafer surfaces having been finished by mirror polishing are scanned with laser light thereby detecting scattered light resulted from particles, scratches, and the like in the front and back surfaces. Further, in order to determine the presence and absence of defects that are hardly determined by an LPD inspection apparatus, appearance inspection is also performed in which the wafer surfaces are examined by visual observation. Since appearance inspection is an organoleptic test, variation in the determination depending on inspectors cannot be avoided, and it takes time for inspectors to master the examination technique. Therefore, there is a demand for establishing an objective inspection method and an automatic inspection method.

To address the above, we have previously proposed in JP 2010-103275 A (PTL 1), as a wafer inspection method, a method of properly evaluating wafers without appearance inspection especially focusing on defects on the rear surface side of the wafer surfaces. Specifically, the method is a method of evaluating the rear surface of a wafer, including: a mapping step of consecutively taking partial images of the rear surface of a wafer in the circumference direction of the wafer and composing the taken partial images to compose a full image of the rear surface of the wafer; and a differentiation step of differentiating the full image to create a differentiated image of the rear surface of the wafer, wherein the wafer is evaluated by detecting unevenly polished portions, haze, scratches, and particles based on the full image or the differentiated image.

An optical system 50 for creating the above full image is described with reference to FIGS. 1A and 1B. FIG. 1B depicts the major part of FIG. 1A for illustrating irradiation light $L_1$ emitted by an annular fiber optic illuminator 51 and reflected light (scattered light) $L_2$. This optical system 50 includes an annular fiber optic illuminator 51, a lens barrel 52, a telecentric lens 53, and a light receiving unit 54. An extra high pressure mercury lamp (wavelength range: 369 nm to 692 nm, output: over 1,000,000 lux) is used for a light source of the annular fiber optic illuminator 51, and a CCD camera is used for the light receiving unit 54. The irradiation light $L_1$ emitted by the annular fiber optic illuminator 51 enters a wafer W at an angle of approximately 20° to the wafer plane and turns into the scattered light $L_2$ upon colliding with a defect D present in the rear surface of the wafer W. The first light receiving unit 54 takes an image upon receiving perpendicular scattered light of the scattered light $L_2$, thereby obtaining and storing the image containing the information of the position of the first optical system 50 and the brightness information of the scattered light.

CITATION LIST

Patent Literature

PTL 1: JP 2010-103275 A

SUMMARY

The inventors considered applying the technique described in PTL 1 to the examination of the state of defects in the back surface of an epitaxial wafer. However, when applying the technique described in PTL 1, as is, to the inspection of the back surface of an epitaxial wafer, not substantially all the defects to be identified by appearance inspection cannot be detected as in an example illustrated in FIG. 2. Note that in the example in FIG. 2, substantially the entire central area of the back surface of the epitaxial wafer except for the periphery area is misidentified as being defective.

Defects in the back surface of an epitaxial wafer may include for example negligible defects such as "pin marks" to be described, "blade scratches", and low scattering "halo", and some defects which are inevitably formed. Accordingly, an apparatus for inspecting the back surface of an epitaxial wafer must not only examine whether defects are formed and the quantity of the defects formed, but also identify the kinds of the defects. In this regard, a conventional appearance examination by visual observation can identify defects in the back surface of an epitaxial wafer to determine the quality of the wafer; however, appearance examination requires evaluation by an inspector as described above. Therefore, there is a demand for establishing a technique of objectively inspecting the back surface of an epitaxial wafer.

In view of the above challenge, it could be helpful to provide an apparatus for inspecting the back surface of an epitaxial wafer, capable of examining defects in the back surface of an epitaxial wafer and a method of inspecting the back surface of an epitaxial wafer using the apparatus.

With a view to achieving the above objective, the inventors made intensive studies. First, the inventors studied what causes defects to be overlooked when the technique described in PTL 1 is applied to the back surface of an epitaxial wafer, whereas the technique can properly evaluate the state of defects of a PW. The inventors analyzed differences between an image of the back surface of an epitaxial wafer obtained by a conventional technique and defects found by appearance examination, and found that in this image, for example, defects of the same or different kinds would overlap one another and even normal portions can be detected as brightness information based on defects. The inventors further studied the cause and found that as compared with the back surface of a PW, part of the back surface of an epitaxial wafer is formed from a source gas that has reached to the back surface, making the surface of the back side rough, which results in irregular reflection because of excessively intensive output of the light source of the above optical system 50, exceeding the capacity of the CCDs. Thus, the inventors ascertained that the misidentification of defects is attributed to the overflow of brightness of the scattered light. Compared with a PW, the surface state of the back surface of an epitaxial wafer is rough (i.e., the haze level of the back surface is bad) due to the haze caused by a source gas that has reached the back surface when an epitaxial layer is formed, and this seems to cause the above-mentioned overflow. Accordingly, even when applied to the examination of the state of defects in the back surface of an epitaxial wafer, the technique described in PTL 1 is considered to overlook defects which can be identified by appearance examination.

Since the surfaces of a PW is less rough unlike the back surface of an epitaxial wafer, when a PW is inspected, an extra high pressure mercury lamp such as a Hg lamp or a metal halide lamp producing light of short wavelengths and high illuminance has been used as a light source of an annular fiber optic illuminator so as to detect even very superficial flaws. However, the overflow would occur on the back surface of the epitaxial wafer as described above. If the illuminance of the super high pressure mercury lamp is reduced to prevent the overflow, which in turn makes the illuminance unstable during the inspection. This being the case, the inventors conceived of using a light source which has relatively low illuminance but can be used in a stable manner for a light source of an annular fiber optic illuminator and found a light source enabling the identification of defects in the back surface of an epitaxial wafer. This discovery led to this disclosure. This disclosure is based on the above findings and studies and we propose the following features.

An apparatus for inspecting a back surface of an epitaxial wafer, according to this disclosure has: an optical system including an annular fiber optic illuminator and an imaging unit which are placed perpendicular to the back surface of an epitaxial wafer; and a scanning unit operating the optical system in parallel with the back surface to scan the back surface. A light source of the annular fiber optic illuminator is composed of either blue LEDs or red LEDs.

Here, the illuminance of the light source is preferably 300,000 lux or more and 1,000,000 lux or less, and the light source is preferably composed of the blue LEDs.

Further, a method of inspecting a back surface of an epitaxial wafer, according to this disclosure includes: an imaging step of consecutively taking partial images of the back surface while operating the optical system to scan the back surface using the scanning unit, with the use of the above apparatus for inspecting a back surface of an epitaxial wafer; an acquisition step of acquiring a full image of the back surface from the partial images; and a detection step of detecting defects present in the back surface from the full image.

In this case, the method preferably further includes, prior to the detection step, an image processing step of image processing the full image; and in the detection step, the detection is preferably performed based on the full image having subjected to the image processing.

Preferably, in the detection step, defects in a periphery of the back surface of the epitaxial wafer are selected, the periphery is segmented into an inner region and an outer region, and defects of the selected defects which are present only in the outer region and have a size exceeding a predetermined threshold value are detected as halos.

Preferably, in the detection step, dot-like defects in the back surface of the epitaxial wafer are selected, and defects of the dot-like defects which have a diameter equal to or larger than a first diameter and equal to or less than a second diameter and have dark part in a center are detected as susceptor pinholes.

Preferably, in the detection step, a dot-like reference defect at a position apart from a center of the back surface of the epitaxial wafer by a predetermined distance is selected, the position of the reference defect is defined as a first reference position, defects in the vicinity of a plurality of second reference positions defined by shifting the first reference position by equal angles around the center are selected, and a group of dot-like defects at the first reference position and in the vicinity of the second reference positions are detected as pin marks.

Also preferably, the method further includes an evaluation step of classifying the selected defects into normal defects and abnormal defects and evaluating whether the abnormal defects are present or not.

Using a suitable light source, this disclosure can provide an apparatus for inspecting the back surface of an epitaxial wafer, capable of detecting defects in the back surface of an epitaxial wafer and a method of inspecting the back surface of an epitaxial wafer using the apparatus.

BRIEF DESCRIPTION OF THE DRAWINGS

In the accompanying drawings:

FIGS. 1A and 1B are schematic views illustrating an optical system of an apparatus for inspecting a back surface of a wafer, used in conventional techniques, in which FIG. 1A is a schematic view illustrating the whole optical system and FIG. 1B is a schematic view illustrating incident light $L_1$ and scattered light $L_2$;

FIGS. 4A to 4D are examples of full images of the back surface of an epitaxial wafer, in which FIG. 4A is a full image obtained using a blue LED light source, FIG. 4B is a full image obtained using a red LED light source, FIG. 4C is a full image obtained using a green LED light source, and FIG. 4D is a full image obtained using a white LED light source;

FIGS. 6A and 6B illustrate a first example of the back surface of an epitaxial wafer, obtained in accordance with one embodiment of this disclosure, in which FIG. 6A is a full image and FIG. 6B is an image obtained by image processing the full image in FIG. 6A;

FIGS. 8A and 8B illustrate a second example of the back surface of an epitaxial wafer, obtained in accordance with one embodiment of this disclosure, in which FIG. 8A is a full image and FIG. 8B is an image obtained by image processing the full image in FIG. 8A;

FIGS. 11A and 11B illustrate a third example of the back surface of an epitaxial wafer, obtained in accordance with one embodiment of this disclosure, in which FIG. 11A is a full image and FIG. 11B is an image obtained by image processing the full image in FIG. 11A; and FIGS. 12A and 12B are schematic views illustrating pin marks which can be detected by one embodiment of this disclosure, in which FIG. 12A depicts a defect PM1 and FIG. 12B depicts a group of defects which are pin marks PM1 to PM3.

DETAILED DESCRIPTION

Figure 3:
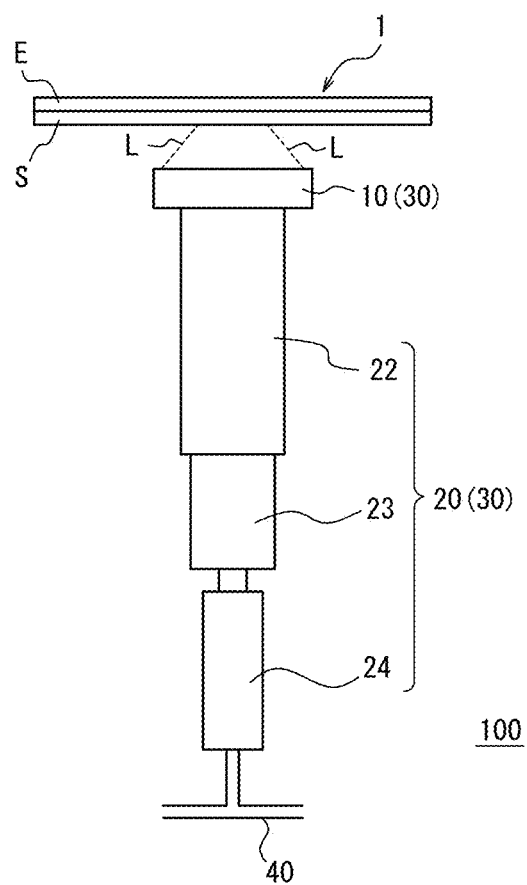
FIG. 3 is a schematic view illustrating an apparatus for inspecting the back surface of an epitaxial wafer according to one embodiment of this disclosure.

Embodiments of this disclosure will now be described with reference to the drawings. FIG. 3 is a schematic view of an epitaxial wafer back surface inspection apparatus 100 according to one embodiment of this disclosure.

(Apparatus for Inspecting Back Surface of Epitaxial Wafer)

As illustrated in FIG. 3, the epitaxial wafer back surface inspection apparatus 100 according to one embodiment of this disclosure has an optical system 30 including an annular fiber optic illuminator 10 and an imaging unit 20 which are placed perpendicular to the back surface of an epitaxial wafer 1; and a scanning unit 40 operating the optical system 30 in parallel with the back surface of the epitaxial wafer 1 to scan the back surface. The light source of the annular fiber optic illuminator 10 is composed of either blue LEDs or red LEDs. The epitaxial wafer 1 in FIG. 3 is obtained by epitaxially growing an epitaxial layer E on a surface of a substrate S. The back surface of the epitaxial wafer 1 is a surface opposite to the side where the epitaxial layer E is formed (in other words, a surface on the side of the substrate S where the epitaxial layer E is not formed, meaning that the surface on the back side of the substrate S is exposed). Details of the structures and steps will now be sequentially described.

The annular fiber optic illuminator 10 used may be a common one; however, the light source is importantly composed of either blue LEDs or red LEDs. The technical significance of this will be described below with reference to FIGS. 4A to 4D. Note that the illuminance of the irradiation light L emitted by the annular fiber optic illuminator 10 is preferably about 300,000 lux to 1,000,000 lux. The angle formed between the irradiation light L and the back surface of the epitaxial wafer 1 is a typical angle, and for example may be about 10° to 30°, or may be roughly 20° or 20° as in conventional techniques.

The structure of the imaging unit 20 is not limited as long as the unit can receive scattered light from the back surface of the epitaxial wafer 1, and the unit can be composed of, for example, a lens barrel 22, a lens 23, and a light receiving unit 24. The lens barrel 22, the lens 23, and the light receiving unit 24 can use commonly used ones. The lens 23 can use, for example, a telecentric lens, and the light receiving unit 24 can use, for example, a CCD camera.

The optical system 30 includes the above-mentioned annular fiber optic illuminator 10 and the imaging unit 20. The back surface of the epitaxial wafer 1 is irradiated using the annular fiber optic illuminator 10, and the optical system 30 receives the scattered light, thereby obtaining partial images of the back surface of the epitaxial wafer 1.

The scanning unit 40 operates the optical system 30 in parallel with the back surface of the epitaxial wafer 1. The scanning unit 40 may operate the optical system 30 in the circumferential direction, vertically, or horizontally. Further, the epitaxial wafer back surface inspection apparatus 100 may have a plurality of (e.g., three) optical systems 30, and each optical system 30 may be operated in the circumferential direction by the scanning unit 40. The scanning unit 40 may be composed of an arm connected to the optical system 30 and a drive stepper motor or a servomotor for actuating the arm, and others.

Figure 4:
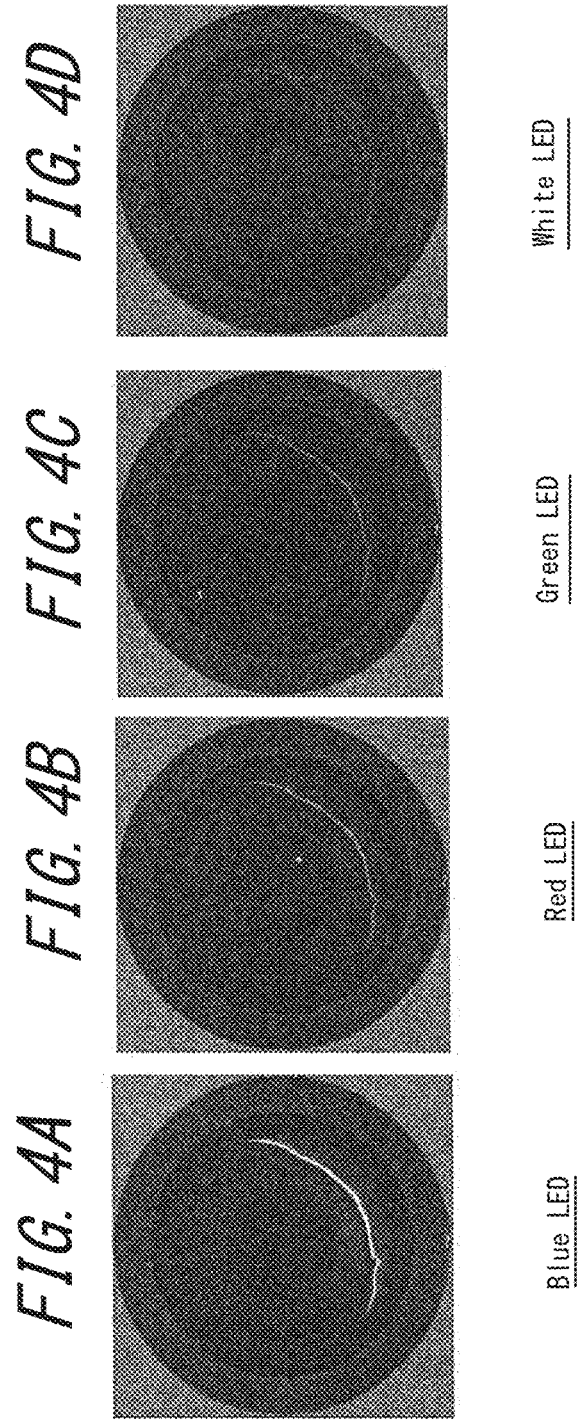

Here, when the light source of the annular fiber optic illuminator 10 of the epitaxial wafer back surface inspection apparatus 100 according to this embodiment uses blue LEDs (irradiation light illuminance: 300,000 lux to 1,000,000 lux, wavelength range: 450 nm to 500 nm, center emission wavelength: 470 µm), partial images of the entire area of the back surface of the epitaxial wafer are consecutively taken and composed to obtain a full image depicting the whole back surface. An example is illustrated in FIG. 4A. Further, a full image of the case where the same back surface is irradiated using a light source of red LEDs (irradiation light illuminance: 300,000 lux to 1,000,000 lux, wavelength range: 600 nm to 700 nm, center emission wavelength: 660 µm) instead of the above blue LEDs is presented in FIG. 4B. Further, a full image of the case using green LEDs (center emission wavelength: 530 µm) having an illuminance comparable to the illuminance of the blue LEDs and red LEDs is presented in FIG. 4C, and a full image of the case using white LEDs (combination of lights from the above blue LEDs, red LEDs, and green LEDs) instead is presented in FIG. 4D.

Scratch-like defects which are defects shaped like arcs are formed in a central area of the full images illustrated in FIGS. 4A to 4D. Further, haze defects are found to be formed around the scratch-like defects in FIGS. 4A and 4B where blue LEDs and red LEDs are used for the respective light sources. In FIGS. 4C and 4D, the scratch-like defects can be identified from the images; however, the haze defects seen in FIGS. 4A and 4B cannot be identified from the images. Further, as is obvious from the comparison of FIGS. 4A to 4D, the highest sensitivity in detecting defects is observed in the case where the blue LEDs are used for the light source. Therefore, blue LEDs are preferably used for the light source of the annular fiber optic illuminator 10 in the epitaxial wafer back surface inspection apparatus 100.

Figure 1A:
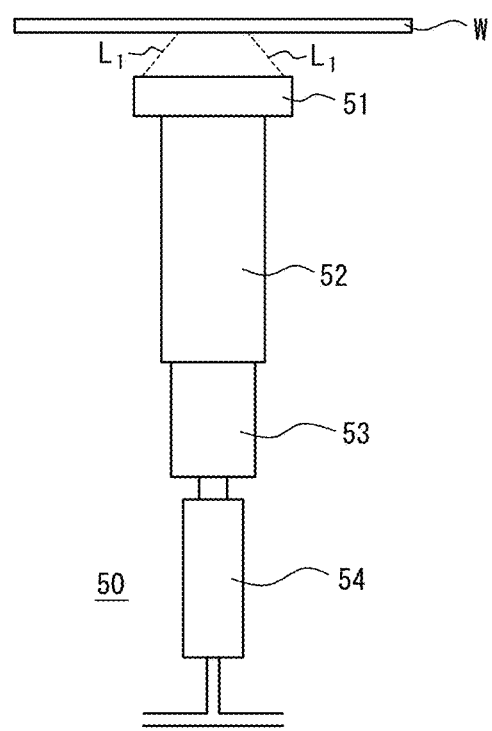
Figure 1B:
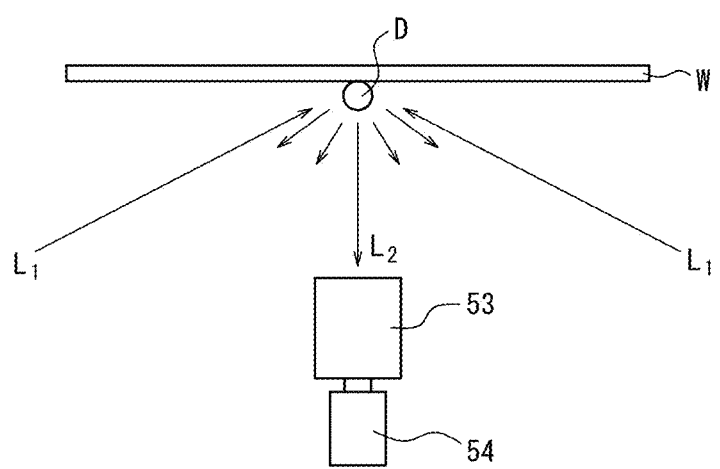
Figure 2:
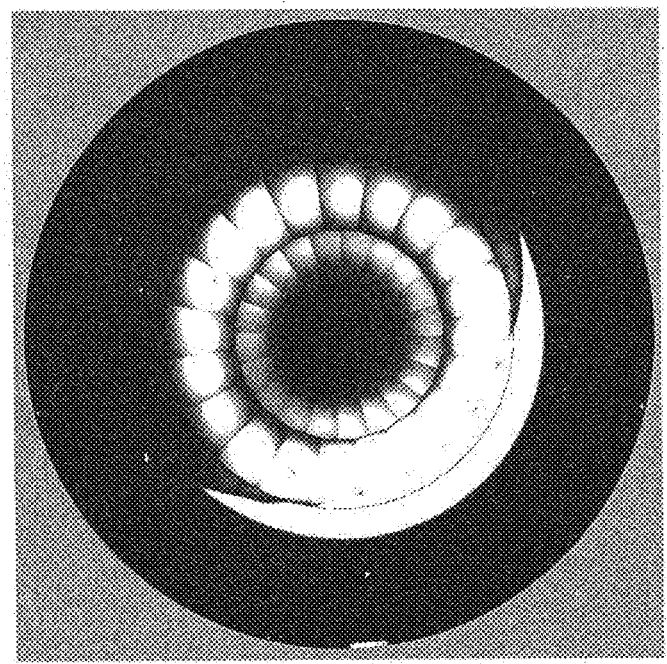
FIG. 2 is an example of a full image of the back surface of an epitaxial wafer, obtained using a wafer inspection apparatus of a conventional technique.

Note that as previously described with reference to FIG. 2, when an extra high pressure mercury lamp (e.g., illuminance: 5,000,000 lux) is used for the light source of the annular fiber optic illuminator 10 as with conventional techniques, the brightness of the defects overflows and the defects cannot be identified.

As described above, the epitaxial wafer back surface inspection apparatus 100 according to this embodiment has good stability although the illuminance is low, and using blue LEDs having a wavelength range of 450 nm to 500 nm or red LEDs having a wavelength range of 600 nm to 700 nm for the light source of the annular fiber optic illuminator 10, an image precisely indicating the state of defects can be acquired even when the back surface of an epitaxial wafer has a bad haze level. This allows defects in the back surface of an epitaxial wafer which could not conventionally been detected by other than visual observation to be detected and identified.

Note that the epitaxial wafer 1 may be an epitaxial silicon wafer obtained by epitaxially growing a silicon epitaxial layer on a surface of a mirror-polished silicon wafer. The epitaxial wafer back surface inspection apparatus 100 according to this embodiment is preferably used for an epitaxial silicon wafer. This is because the above described bad haze level on back surface becomes a problem.

(Method of Inspecting Back Surface of Epitaxial Wafer)

Figure 5:
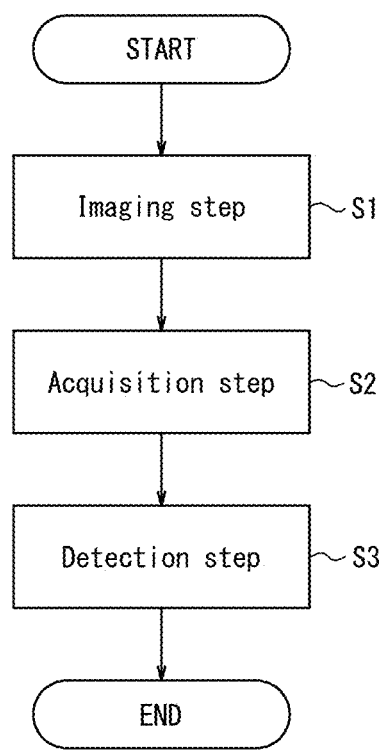
FIG. 5 is a flowchart illustrating a method of inspecting the back surface of an epitaxial wafer according to one embodiment of this disclosure.

Next, one embodiment of a method of inspecting the back surface of an epitaxial wafer using the above-described epitaxial wafer back surface inspection apparatus 100 will be described. As illustrated in FIG. 5, this embodiment includes an imaging step S1 of consecutively taking partial images of the back surface of the epitaxial wafer 1 while operating the optical system 30 to scan the back surface using the scanning unit 40; an acquisition step S2 of acquiring a full image of the back surface of the epitaxial wafer 1 from the partial images; and a detection step S3 of detecting defects present in the back surface of the epitaxial wafer 1 from the resulting full image.

Specifically, in the imaging step S1, first, a partial image of the back surface of the epitaxial wafer 1 is taken when the optical system 30 is located at a predetermined position. Subsequently, the scanning unit 40 operates the optical system 30 to scan a position different from the above predetermined position to take another partial image of the back surface of the epitaxial wafer 1. For example, the back surface of the epitaxial wafer 1 is segmented into 100 to 200 segments, and the imaging and scanning are repeated for the respective segments thus consecutively taking partial images of the back surface of the epitaxial wafer 1 (S1). Next, all the partial images taken are composed to obtain a full image of the back surface of the epitaxial wafer 1 (S2). An example of the resulting full image is presented in FIG. 4A described above, for example.

Next, the detection step S3 of detecting defects present in the back surface of the epitaxial wafer 1 from the full image acquired in the above-mentioned acquisition step S2 is performed. In the back surface of the epitaxial wafer 1, specific defect patterns are formed depending on the causes of the defects, for example, some defects may be caused by a source gas that has reached the back surface when the epitaxial layer is formed, and some defects may be due to contact with a susceptor supporting the epitaxial wafer 1 in an epitaxial growth furnace. Further, the formation position (a central area in the back surface, a periphery of the back surface, randomly formed in the entire back surface, etc.), the defect pattern length, the aspect ratio, and the unique combination of dot-like defects (hereinafter collectively referred to as "defect patterns") are specific to the causes of the defects. In this step, conditions for these defect patterns specific to the different kinds of defects are set, and defects meeting the conditions are detected from the full image. Thus, the defects present in the back surface of the epitaxial wafer 1 can be detected.

Note that prior to the detection step S3, an image processing step of image processing the acquired full image is preferably performed. The detection step S3 is preferably then performed based on the image processed full image. In the image processing step, for example, when a differentiated image is acquired from the full image, the influence of noise and the like can be reduced, so that the defects present in the back surface of the epitaxial wafer 1 can be detected more accurately. When the full image of FIG. 6A to be described is differentiated and subjected to a thinning process, the image of FIG. 6B is obtained. This correspondence also applies to FIGS. 8A and 8B and FIGS. 11A and 11B. Using the image processed full image can increase the accuracy in detecting defects in the back surface of the the epitaxial wafer 1 can be increased.

Aspects of specific methods of detecting "halo", "susceptor pinholes", and "pin marks" formed in the back surface of the epitaxial wafer 1 will be described below. These aspects of detecting defects are merely for illustrative purposes only, and defects other than the above three kinds of defects can also be detected by an embodiment according to a method of this disclosure by applying defect patterns specific to different kinds of defects.

<Halo>

Figure 6A:
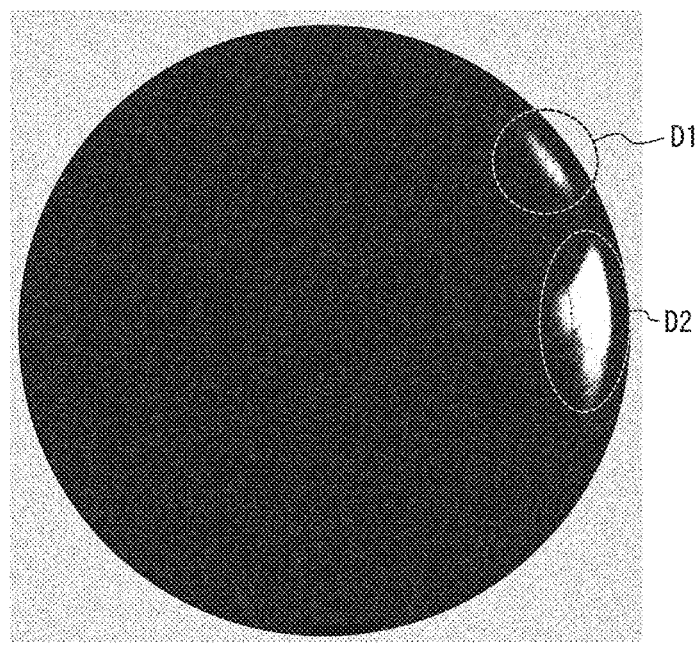
Figure 6B:
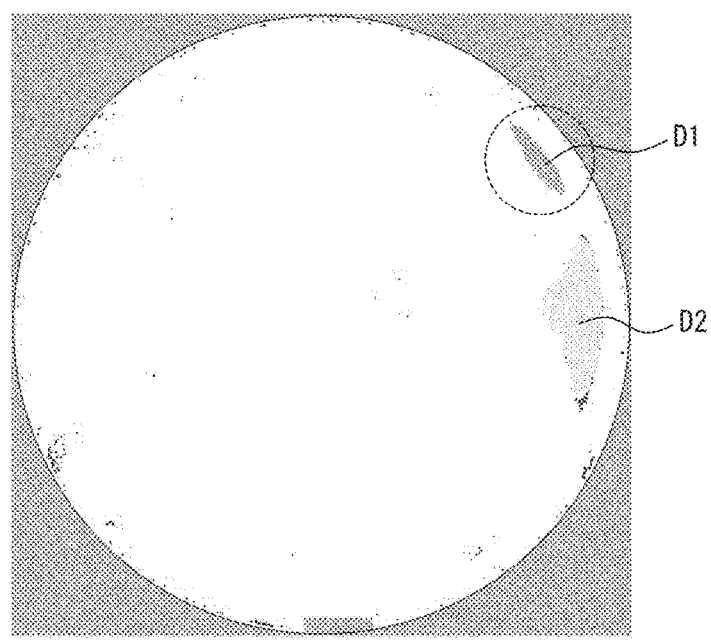

As a first example of defects, FIG. 6A presents a full image of the back surface of the epitaxial wafer 1 where a halo D1 is formed, the full image having been acquired using the epitaxial wafer back surface inspection apparatus 100 according to this disclosure. FIG. 6B presents an image obtained by image processing FIG. 6A. Note that a haze defect D2 is also formed in the back surface of the epitaxial wafer 1.

"halo" herein means a defect having a pattern like an etch pattern, formed in the periphery of the back surface of the epitaxial wafer by epitaxial growth.

Figure 7:
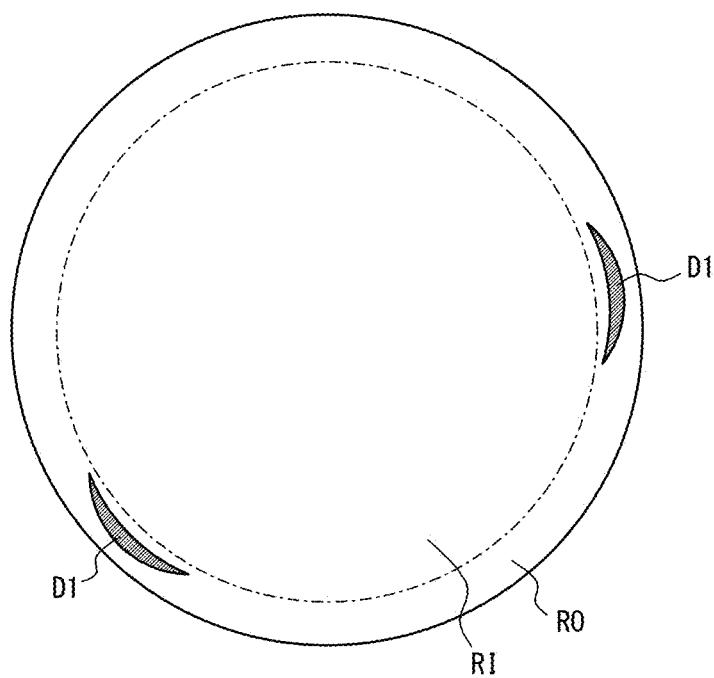
FIG. 7 is a schematic view illustrating halos which can be detected by one embodiment of this disclosure.

An aspect of detecting the above halo D1 in one embodiment of the inspection method according to this disclosure will be described with reference to FIG. 7. In FIG. 7, two halos D1 are formed in the periphery of the back surface of the epitaxial wafer 1. In the detection step S3, first, defects in the periphery of the back surface of the epitaxial wafer 1 are selected. The periphery of the back surface of the epitaxial wafer is segmented into an inner region RI and an outer region RO based on a predetermined radius. Of the selected defects, defects which are present only in the outer region RO and have a size exceeding a predetermined threshold value can be detected as "halos". In determining the size of the defects, a specific threshold value may be set for the brightness. Note that defects formed across the outer region RO and the inner region RI can be detected as haze defects D2 rather than as halos D1. Thus, when halos D1 are detected, the epitaxial wafer is evaluated to have halos D1 in its back surface.

<Susceptor Pinhole>

Figure 8A:
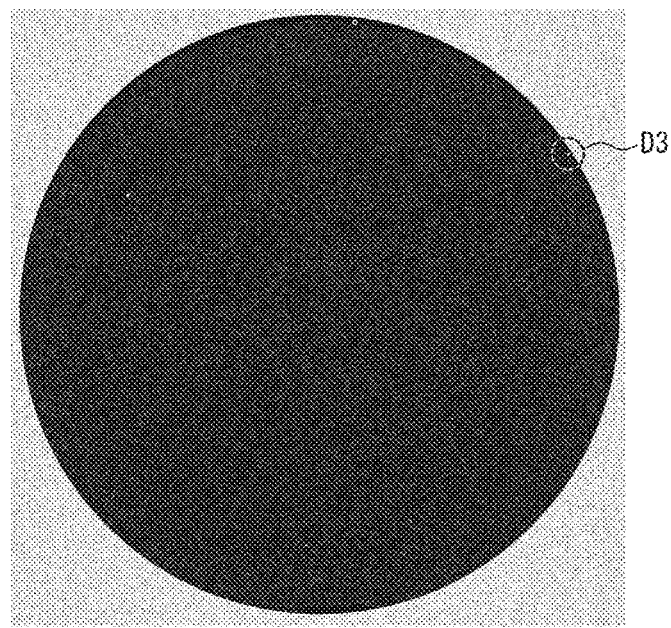
Figure 8B:
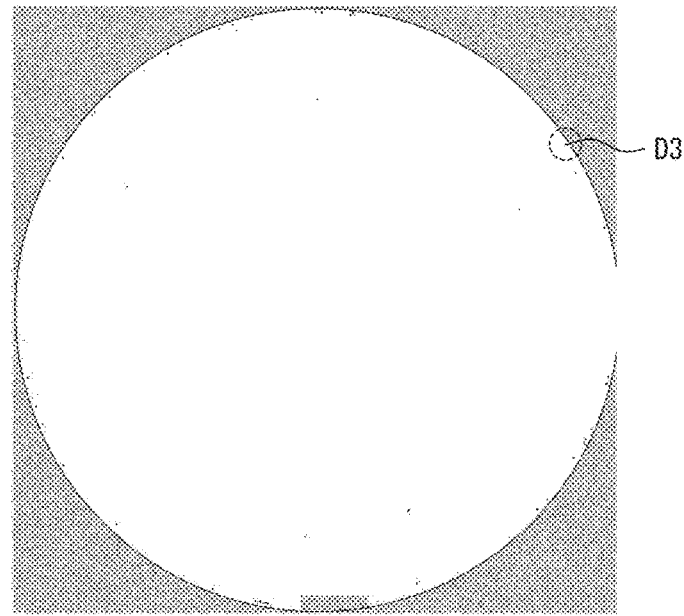
Figure 9A:
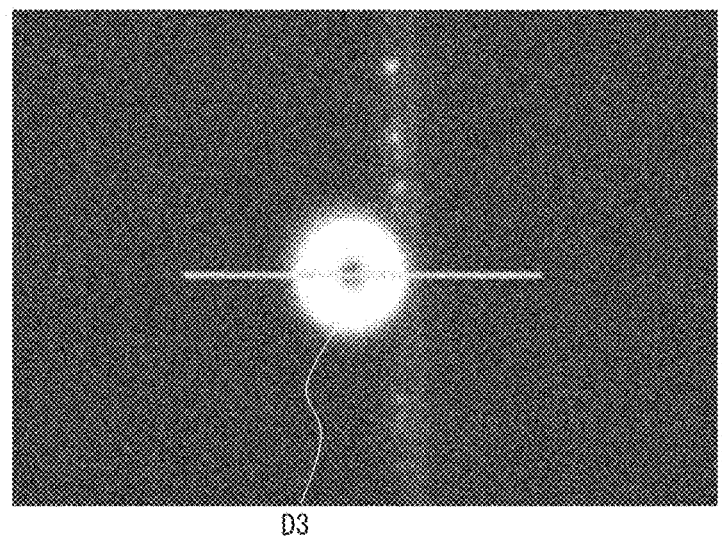
FIG. 9A is a magnified image of the susceptor pinhole in FIG. 8A
Figure 9B:
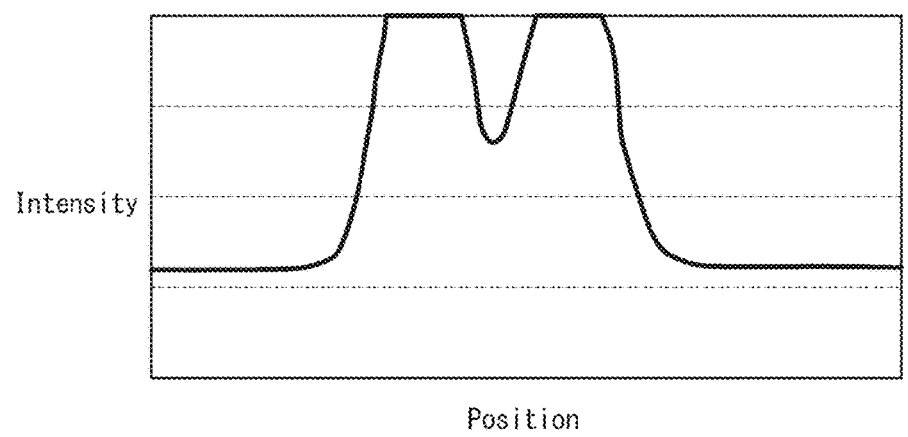
FIG. 9B is a graph indicating the intensity profile thereof.

As a second example of defects, FIG. 8A presents a full image of the back surface of the epitaxial wafer 1 in which a susceptor pinhole D3 is formed, the full image having been acquired using the epitaxial wafer back surface inspection apparatus 100 according to this disclosure. FIG. 8B presents an image obtained by image processing FIG. 8A. Further, FIG. 9A presents a magnified image of the vicinity of the susceptor pinhole D3 in FIG. 8A. FIG. 9B illustrates the intensity (brightness) profile of the susceptor pinhole D3. As in the specific example illustrated in FIGS. 9A and 9B, a susceptor pinhole is a substantially circular dot-like defect, and has a dark part in the central area.

"Susceptor pinhole" herein means a defect visible as haze with a core, which is a trace of a pinhole formed by a susceptor during epitaxial growth, transferred onto the back surface of the epitaxial wafer. Therefore, the outer diameter of a susceptor pinhole is in a predetermined range.

Figure 10:
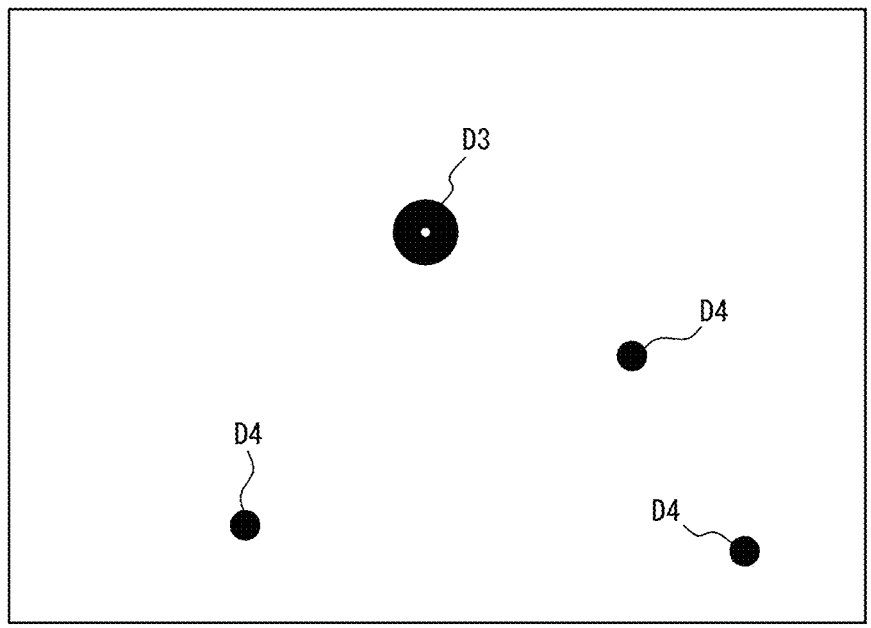
FIG. 10 is a schematic view illustrating a susceptor pinhole which can be detected by one embodiment of this disclosure.

An aspect of detecting the above susceptor pinhole D3 in one embodiment of the inspection method according to this disclosure will be described with reference to FIG. 10. In the detection step S3, dot-like defects in the periphery of the back surface of the epitaxial wafer 1 are selected. A first radius and a second radius (where [second radius]>[first radius]) are previously set as threshold values to include the outer diameter of the susceptor pinhole, and defects of the selected dot-like defects, which have a radius equal to or more than the first radius and equal to or less than the second radius are further selected. Of such dot-like defects, a defect having a dark center can be detected as a "susceptor pinhole". Note that dot-like defects D4 having a size with a radius smaller than the first radius (although depending on the formation) may be identified as particles.

<Pin Marks>

Figure 11A:
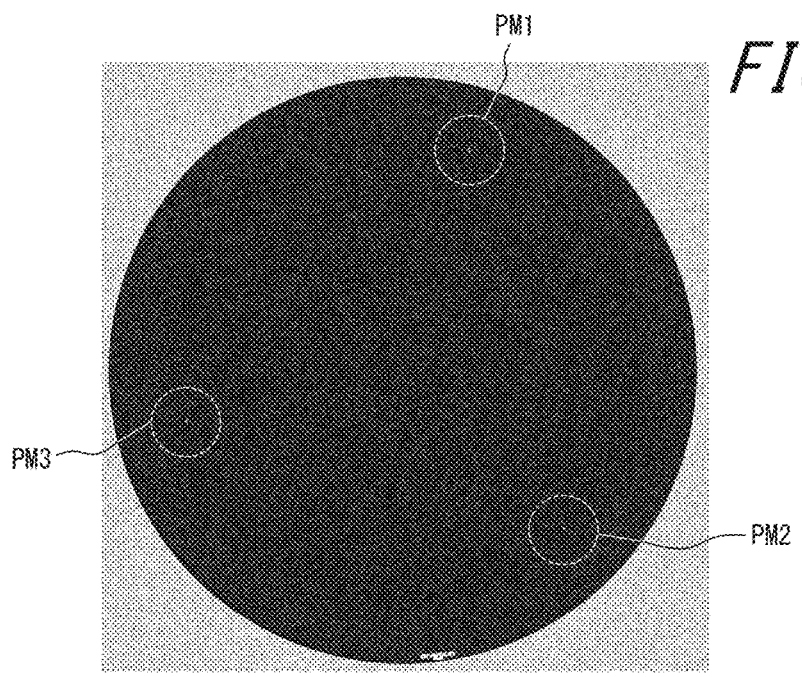
Figure 11B:
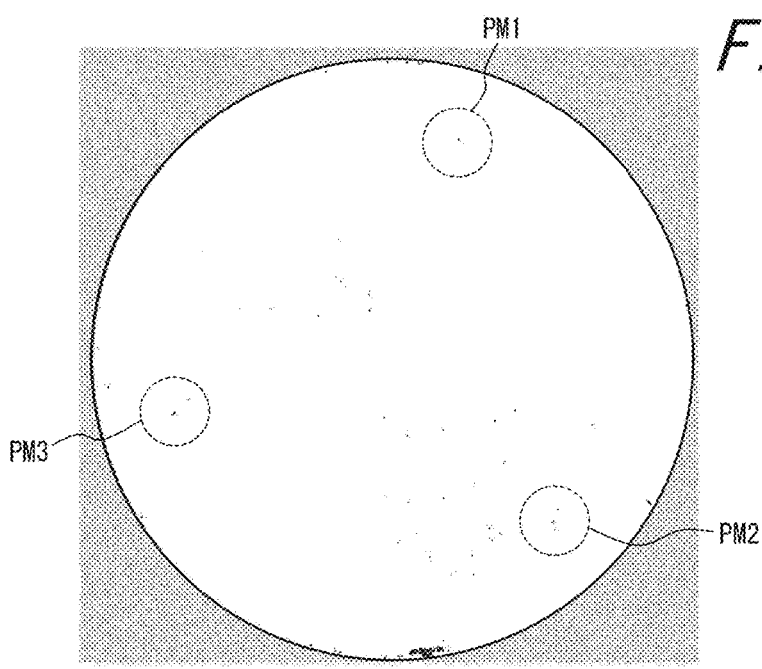

As a third example of defects, FIG. 11A presents a full image of the back surface of the epitaxial wafer 1 in which pin marks PM1 to PM3 are formed, the full image having been acquired using the epitaxial wafer back surface inspection apparatus 100 according to this disclosure. FIG. 11B presents an image obtained by image processing FIG. 11A.

"Pin marks" herein mean defects constituted by a group of minute flaws like wear marks formed in the periphery of the back surface of an epitaxial wafer, which are caused in accordance with the shape of the wafer lift pins or due to contact between the pin and the wafer and are specific to the case where a certain epitaxial furnace (Centura series manufactured by Applied Materials, Inc.) is used; or defects formed from attached matter. Although depending on the shape of the wafer lift pins, for example, pin marks which can be formed at three positions are always formed at three positions at the same time, in which case, the positions are 120° apart from one another around the center of the back surface of the epitaxial wafer. Further, pin marks are present within a range of a predetermined radius depending on the shape of the lift pins, and the defects of the pin marks form circular light points.

Figure 12A:
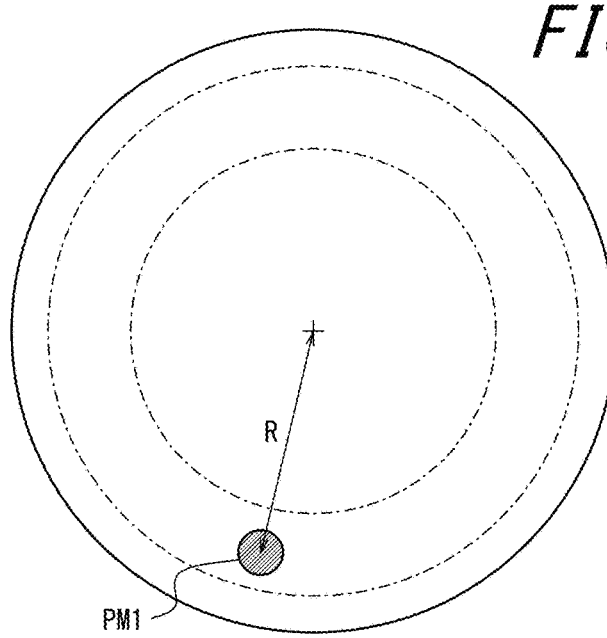
Figure 12B:
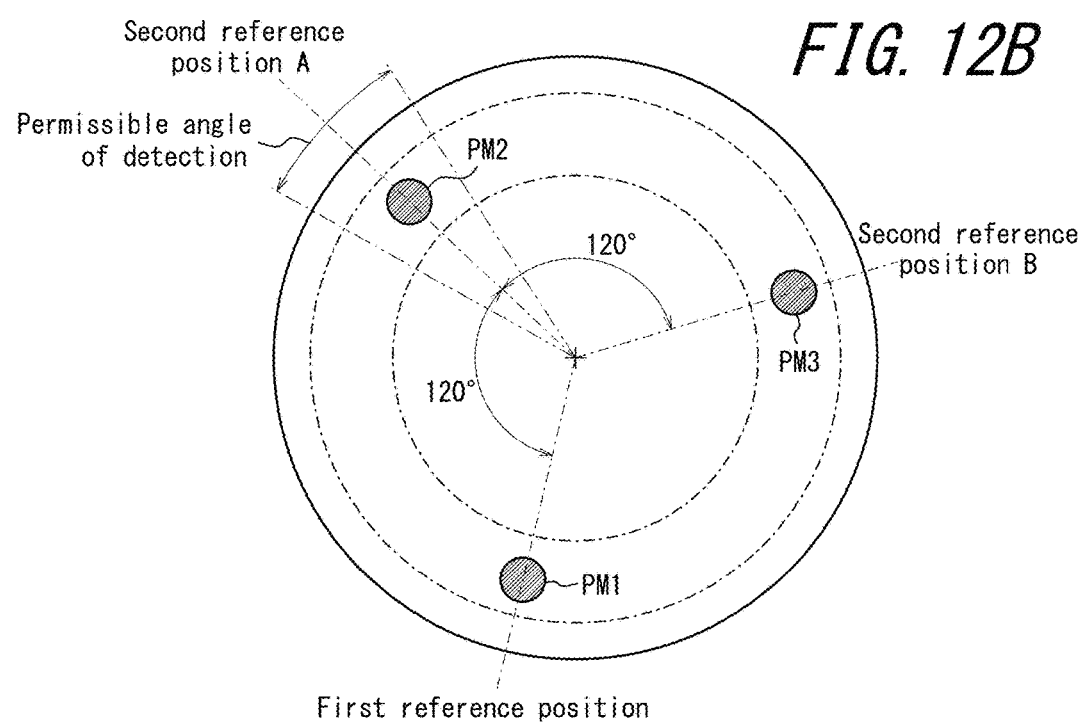

An aspect of detecting the above pin marks PM1 to PM3 in one embodiment of the inspection method according to this disclosure will be described with reference to FIGS. 12A and 12B. In the detection step S3, first, a dot-like reference defect PM1 at a position apart from the center of the epitaxial wafer by a predetermined distance R is selected (FIG. 12A). The position of the reference defect PM1 is defined as a first reference position, the first reference position is shifted around the center by equal angles (by 120° in the example of FIGS. 12A and 12B, since three pin marks are formed), and defects in the vicinity of a plurality of second reference positions A and B are selected. Since the formation position of pin marks may slightly deviate from the equal angular intervals, a permissible angle of detection may be set (FIG. 12B). In this case, defects within the permissible angle of detection are regarded as the defects "in the vicinity". The defects PM1 to PM3 at the first reference position and in the vicinity of the second reference positions A and B can be detected as "pin marks".

This embodiment preferably further includes, after the detection step S3, an evaluation step of classifying the selected defects into normal defects and abnormal defects and evaluating whether the abnormal defects are present or not. As described above, the back surface of an epitaxial wafer has negligible defects such as pin marks. Therefore, to evaluate the quality of the back surface of an epitaxial wafer, the presence or absence of abnormal defects is preferably determined. The kinds and the quantity of abnormal defects may be evaluated qualitatively or quantitatively.

Although the embodiments of this disclosure have been described above, the embodiments are illustrated only as representative examples, and therefore this disclosure is not limited thereto and may be changed in various manners within the spirit of this disclosure.

INDUSTRIAL APPLICABILITY

This disclosure can provide an apparatus for inspecting the back surface of an epitaxial wafer, capable of examining defects in the back surface of an epitaxial wafer and a method of inspecting the back surface of an epitaxial wafer using the apparatus.

REFERENCE SIGNS LIST

1: Epitaxial wafer
10: Annular fiber optic illuminator
20: Imaging unit
30: Optical system
40: Scanning unit
100: Epitaxial wafer back surface inspection apparatus
D: Defect

The invention claimed is:

1. An apparatus for inspecting a back surface of an epitaxial wafer, comprising:
   an optical system including an annular fiber optic illuminator and an imager which are placed perpendicular to a back surface of an epitaxial wafer; and
   a scanner operating the optical system in parallel with the back surface to scan the back surface,
   wherein a light source of the annular fiber optic illuminator is composed of either blue LEDs or red LEDs.

2. The apparatus for inspecting a back surface of an epitaxial wafer, according to claim 1, wherein an illuminance of the light source is 300,000 lux or more and 1,000,000 lux or less.

3. The apparatus for inspecting a back surface of an epitaxial wafer, according to claim 1, wherein the light source is composed of the blue LEDs.

4. A method of inspecting a back surface of an epitaxial wafer, comprising:
   consecutively taking partial images of the back surface while operating the optical system to scan the back surface using the scanner, with the use of the apparatus for inspecting a back surface of an epitaxial wafer, according to claim 1;
   acquiring a full image of the back surface from the partial images; and
   detecting defects present in the back surface from the full image.

5. The method of inspecting a back surface of an epitaxial wafer, according to claim 4, further comprising, prior to the detecting defects, image processing the full image,
   wherein in the detecting defects, the detection is performed based on the full image having subjected to the image processing.

6. The method of inspecting a back surface of an epitaxial wafer, according to claim 4, wherein in the detecting defects, defects in a periphery of the back surface of the epitaxial wafer are selected, the periphery is segmented into an inner region and an outer region, and defects of the selected defects which are present only in the outer region and have a size exceeding a predetermined threshold value are detected as halos.

7. The method of inspecting a back surface of an epitaxial wafer, according to claim 4, wherein in the detecting defects, dot-like defects in the back surface of the epitaxial wafer are selected, and a defect of the dot-like defects which has a diameter equal to or larger than a first diameter and equal to or less than a second diameter and has dark part in a center is detected as a susceptor pinhole.

8. The method of inspecting a back surface of an epitaxial wafer, according to claim 4, wherein in the detecting defects, a dot-like reference defect at a position apart from a center of the back surface of the epitaxial wafer by a predetermined distance is selected, the position of the reference defect is defined as a first reference position, defects in the vicinity of a plurality of second reference positions defined by shifting the first reference position by equal angles around the center are selected, and a group of dot-like defects at the first reference position and in the vicinity of the second reference positions are detected as pin marks.

9. The method of inspecting a back surface of an epitaxial wafer, according to claim 4, further comprising classifying the selected defects into normal defects and abnormal defects and evaluating whether the abnormal defects are present.

* * * * *